United States Patent [19]

Sullivan, III et al.

[11] 4,231,956
[45] Nov. 4, 1980

[54] PROCESS FOR PREPARATION OF THIOETHERS

[75] Inventors: Daniel S. Sullivan, III; Wilbur L. Bridges, both of Houston, Tex.

[73] Assignee: Exxon Research & Engineering Co., Florham Park, N.J.

[21] Appl. No.: 937,316

[22] Filed: Aug. 28, 1978

Related U.S. Application Data

[63] Continuation of Ser. No. 776,261, Mar. 10, 1977, abandoned, which is a continuation of Ser. No. 599,998, Jul. 29, 1975, abandoned.

[51] Int. Cl.³ .................. C07C 120/00; C07C 121/16; C07C 121/20; C07C 149/20
[52] U.S. Cl. .......................... 260/465.8 R; 260/465.1; 260/346.74; 560/152; 560/154; 564/192
[58] Field of Search .................... 260/609 B, 465.8 R, 260/405.1, 481 R, 561 S; 560/152, 154

[56] References Cited

U.S. PATENT DOCUMENTS

| | | | |
|---|---|---|---|
| 2,163,176 | 6/1939 | Keyssner | 560/154 |
| 2,268,185 | 12/1941 | Burke et al. | 260/481 R |
| 2,416,052 | 2/1947 | Gribbins | 560/152 |
| 3,194,830 | 7/1965 | Dann et al. | 560/152 |
| 3,502,708 | 3/1970 | Thoma et al. | 260/465.1 |
| 4,052,440 | 10/1977 | Gladstone et al. | 560/154 |

FOREIGN PATENT DOCUMENTS 891391 9/1953 Fed. Rep. of Germany .......... 560/152

Primary Examiner—Joseph Paul Brust

[57] ABSTRACT

The process of preparing thioethers by reacting aliphatic thioalcohols, e.g., mercaptans, including hydrogen sulfide with activated, alpha, beta unsaturated compounds

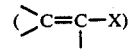

capable of participating in the Michael Addition Rection* in which X is a suitable electron withdrawing group. The Addition, which is carried out in the presence of a catalytic base is greatly improved with respect to minimizing formation of side products by utilizing a specially selected catalyst comprising one or more cyclic tertiary nitrogen compounds having an excellent balance between reactivity and selectivity. The preparation of thioethers from acrylic acid derivatives especially esters ($CH_2=CH-COOR'$, $R'=C_1-C_8$) is preferred. The preparation of the dimethyl ester of 3,3'-thiodipropionic acid to result in dimethylthiodipropionate of relatively high purity is especially preferred.

* See Vogel, PRACTICAL ORGANIC CHEMISTRY, p. 912-913, Third Enlarged Edition.

9 Claims, 8 Drawing Figures

PROCESS FOR PREPARATION OF THIOETHERS

CROSS-REFERENCE TO RELATED APPLICATIONS

This application is a continuation of Ser. No. 776,261, filed Mar. 10, 1977, now abandoned, which in turn is a continuation of Ser. No. 599,998, filed July 29, 1975, now abandoned. The benefit of the filing dates of said applications is hereby claimed.

BACKGROUND OF THE INVENTION

Many hydrocarbons, including foods, lubricants and fuels, and substituted hydrocarbons, particularly polyolefin polymers and other plastics, are susceptible to oxidative and photo-initiated degradation. Conventionally, this degradation is retarded by utilizing additives which are termed "antioxidants" and "UV stabilizers", respectively. Polymers made from olefins are especially susceptible to oxidative degradation.

Low density polyethylene usually requires only a small amount of antioxidant and polystyrene likewise requires only a minimal amount of antioxidants. Nevertheless, high density polyethylene, high impact polystyrene, ABS terpolymers and polypropylene are included among commercial polymers which are exceedingly sensitive to oxidative degradation both while being processed and upon exposure to the environment.

It is generally accepted that polymer degradation by free radicals in the presence of oxygen involves chain scission followed by termination. Chain scission results in loss of molecular weight, increased melt flow, a decrease of polymeric roughness, some cross-linking and an eventual disintegration to powder.

Cross-linking results in an increase of molecular weight, embrittlement and a decrease in melt flow.

It is apparent that many polymers will have to be exposed to heat, both during processing and during their life in a particular use, and oxygen will also be unavoidable in these applications. Therefore, the adverse effect of degradation must be minimized in order to obtain a reasonable service life for the polymer material.

A great many compounds for stabilizing polyolefins have been developed with the object of retarding, inhibiting or otherwise modifying the degradation process. People disagree as to exactly how these stabilizers function.

There is general agreement that one class of materials prevents adverse degradation by oxidation by acting by a free radical scavenging mechanism. Examples of these are hindered phenols and amines.

Another type acts as peroxide decomposers which actually decompose the peroxides formed on the polymer backbone. Classes of compounds which appear to work in this manner are thioesters and phosphites.

Thioesters and alkyl aryl phosphates are generally used in combination with the hindered phenols and appear to interact with them to increase the overall stability in a synergistic manner although their primary function is apparently as peroxide decomposers.

Synergistic mixtures of alkylated phenols, or alkylidene-bis-alkylated phenols, and sulfur compounds have achieved active commercial success. For instance, dilaurylthiodipropionate has been used extensively commercially as the sulfur component of the synergistic mixture. Distearylthiodipropionate (DSTDP) is somewhat better as a synergist and is also gaining commercial acceptance.

Dimethylthiodipropionate is exceptionally useful as a synthetic intermediate to prepare a wide variety of such higher diesters. These higher diesters are conveniently prepared by transesterification. Thus, distearylthiodipropionate, dilaurylthiodipropionate, diabietylthiodipropionate, and the like, have all been conveniently prepared by transesterification from dimethylthiodipropionate.

Such higher diesters are not only extremely useful as a synergist antioxidant for various hydrocarbons, but they are also extremely useful as plasticizers/heat stabilizers for vinyl chloride polymers and synthetic rubbers.

They can be used as corrosion inhibitors. Not only are they stabilizers for polyolefins, but they are also antioxidants for food, cosmetics, lubricants, pharmaceuticals, and soaps.

Thus dimethylthiodipropionate is an extremely useful intermediate to prepare compounds of acknowledged utility for a great many well-defined, well-established end uses.

Nevertheless, the conventional synthesis of dimethylthiodipropionate suffers from a severe drawback that fairly large quantities of side products are produced. These side products adversely affect the color of the product and must be removed by expensive and difficult procedures such as vacuum distillation, solvent extraction or washing, etc.

SUMMARY OF THE INVENTION

The synthesis of thioethers from aliphatic mercaptans, preferably hydrogen sulfide and activated, alpha, beta unsaturated Michael Acceptors is considerably improved by utilizing a basic catalyst comprising a cyclic ring containing one or more non-hindered nitrogen atoms within the ring thus avoiding the formation of undesirable intermediate and side products in the primary reaction.

DESCRIPTION OF THE PREFERRED EMBODIMENTS

Figure 1:
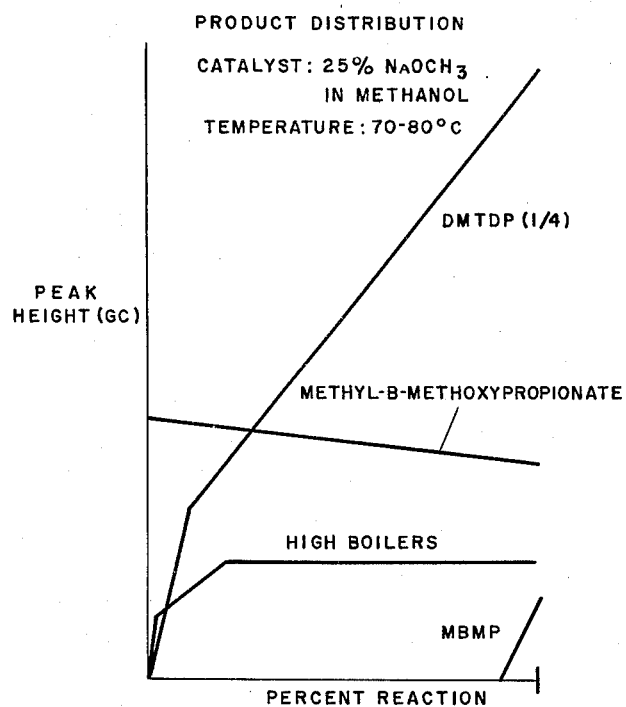
FIG. 1 shows the undesirable product distribution in the synthesis of dimethylthiodipropionate (DMTDP) utilizing a standard catalyst of the art from Example 1.

It has been discovered and forms the substantial conceptual basis of this invention that extraordinary process and product benefits can be obtained in a reaction leading to thioethers through the use of specific, novel and unobvious compounds as catalysts. These catalysts show an exceptional increase in selectivity over previous catalysts taught in the art. For instance, catalysts of the art comprise sodium methoxide, trimethyl benzyl ammonium hydroxide, trimethyl benzyl ammonium methoxide, and the like. All of these catalysts are basic, but result in the formation of highly deleterious by-products in the reaction mixture in addition to the desired thioether.

Triethyl amine is an example of a catalyst known to the art which is somewhat more selective to reduce some by-products, but substantially less reactive to the point that unsatisfactory results are produced even with a five fold increase in the catalyst usage rate.

Thus the process of the invention utilizes in a novel manner certain cyclic unhindered nitrogen compounds, which are not only exceptionally selective to produce the desired thioethers with greatly reduced quantities of by-products, but they are reactive enough to promote the desired reaction at an acceptable rate when present in low concentrations.

Although the invention will be described in detail in connection with the most preferred species of thioether, e.g., dimethylthiodipropionate, and the preferred process for producing it, which is the reaction of $H_2S$ with methyl acrylate in the presence of bicyclic compounds containing at least one tertiary unhindered nitrogen atom, it will be apparent that the invention in its broadest sense encompasses a generic process concept of considerable scope.

In the broad sense, the invention comprises a novel, improved process for preparing thioethers of the formulas R—S—R or R'—S—R by the addition of hydrogen sulfide ($H_2S$) of R'SH where R'=alkyl or aryl to a suitable alpha, beta unsaturated Michael Acceptor of the type

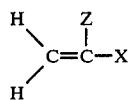

in which Z=H or —$CH_3$ and X is a suitable electron withdrawing group, preferably carboalkoxy or nitrile, but other suitable groups, for example carboxamide, would be applicable. R' is a $C_1$ to $C_{50}$, preferably $C_1$ to $C_{18}$, most preferably $C_1$ to $C_8$, hydrocarbon or substituted hydrocarbon, preferably an alkyl, aryl, alkaryl or substituted derivative thereof. The most preferred Michael Acceptors are methyl acrylate, ethyl acrylate, acrylonitrile, methyl methacrylate, ethyl methacrylate, methacrylonitrile, acrylamide, maleic anhydride, butyl acrylate and methacrylate, and amyl acrylate and methacrylate.

R is

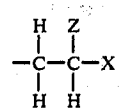

where X and Z have the meanings described above.

The characteristics of the conventional reaction are that mercaptans having the formula R'SH in which R' is H or a $C_1$ to $C_{18}$, preferably $C_1$ to $C_8$ alkyl group, are added to a suitable alpha, beta unsaturated Michael Acceptor in the presence of a relatively strong base, such as those itemized above. The reaction is exothermic. Following the reaction, the catalyst is neutralized. And the desired thioether must normally be obtained by vacuum distillation because of the presence of numerous impurities. The reaction for the synthesis of dimethylthiodipropionate using $H_2S$ which is the preferred mercaptan for this invention is illustrated below as follows:

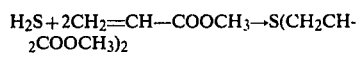

In this reaction, one would expect and it does occur with the conventional catalyst that the reaction mixture would have the following contaminants and by-products: methylacrylate, hydrogen sulfide, methyl-beta-mercaptopropionate and methyl-beta-methoxypropionate. Various polymerization products and Diekmann products, which are cyclic compounds, and other trace quantities are also expected.

There are other impurities which were observed by gas chromatography which were not identified chemically.

Equations detailing a typical reaction of mercaptan with an ester of acrylic acid in the presence of the catalyst of the invention are set forth below:

Ideally, it would be desirable to ascertain reaction conditions which are sufficiently strong to allow the intended reactions to go to completion, but mild enough to avoid side reactions.

It was found that in order to achieve these objectives, the use of a proper catalyst representing a delicate balance between reactivity and selectivity was critical. In general, it was found that the catalyst class comprising bicyclic compounds containing at least one unhindered tertiary nitrogen atom were extremely effective. Such compounds containing either 1 or 2 nitrogen atoms are preferred. These can also be designated as cyclic amidines, azabicycloenes and azacyclines. It was found that the following bicyclic compounds, abbreviated as DBN, DBU, and DABCO, were particularly effective:

1,5-Diazabicyclo(4,3,0) non-5-ene (DBN) 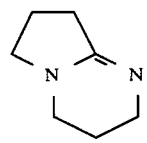

1,5-Diazabicyclo(5,4,0) undec-5-ene (DBU) 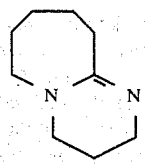

1,4-Diazabicyclo(2,2,2)octane (DABCO) 

Thus, compounds of this nature having the general formula

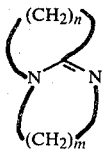

where n=3, 4, 5, 6, 7, 8 and m=2, 3, 4, 5, 6, characterize the general class of effective catalysts. A specific named example of this type of catalyst, in addition to those specifically identified above, is quinuclidine:

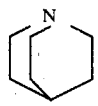

As has been mentioned above, dimethylthiodipropionate is an extremely useful precursor of higher diesters. Higher diesters of particular interest for synergistic antioxidants include the following:

Distearylthiodipropionate: $S(CH_2CH_2COOC_{18}H_{37})_2$
Diabiethylthiodipropionate: $S(CH_2CH_2COOR)_2$
where R is

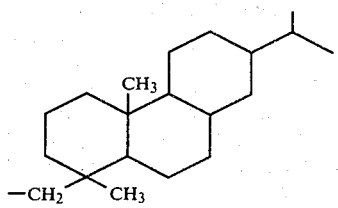

Some generalized factors regarding the criteria governing the selection of the effective catalyst of the invention also include the fact that the catalysts are strong bases. They contain one or more tertiary sterically unhindered nitrogen atoms in the ring structure. Thus, there are no alkyl group barriers to the lone pair of electrons on each nitrogen atom.

Thus, compounds such as 2,6-dialkylpyridines having the following formula

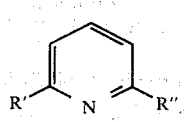

and N,N-dialkylanilines having the following formula

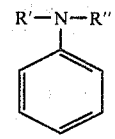

where R' and R" are alkyl groups or hydrogen are not useful for the purposes of the invention. These are hindered catalysts of relative low basicity. They do not have the requisite activity for this type of preparation.

In general, the catalyst can be used in functional catalytic quantities sufficient to give yields desired with minimal size reaction products.

In general, from 0.001 to 1.5, preferably 0.001 to 0.3, most preferably 0.01 to 0.3 wt. percent of catalyst will be used based on unsaturated compound.

Very generally speaking, the temperature conditions can range over a wide spectrum. But in general, 30° to 90° C., preferably 60° to 80° C., will give satisfactory results.

A preferred process for synthesizing dimethylthiodipropionate in a semi-commercial batch process is summarized as follows:

Sequence of Process Steps

The exact sequence of steps during the reaction stage of the process as well as the sequence and selection or omission of certain steps in the work-up stage of a proposed process can have a profound influence on the economics and desirability of a process. Summarized below are some of the steps which are recommended for this process.

Reaction Steps (1) Reactor should be thoroughly cleaned and inspected before changing.

This is to prevent contamination of the product or neutralization of the catalyst. Both glass lined and stainless steel reactors are suitable.

(2) Charge methyl acrylate into the reactor.

(3) Agitate the methyl acrylate and add 0.2 wt. % of 1,4 diazabicyclo (2.2.2) octane to the methyl acrylate. Seal the reactor.

This is an important advantage of this catalyst over sodium methoxide in that DABCO can be added before $H_2S$ addition is begun. The reaction can be followed by watching the pressure drop in a sealed reactor.

(4) Hydrogen sulfide is then charged into the reactor so that it can percolate through the bulk of the fluid. It is important to maintain maximum agitation to insure complete absorption.

(5) Maintain the temperature at CA 40°–50° C. If required for a suitable reaction rate a running temperature of 60° C. could be employed, however the lowest temperature which gives a suitably fast reaction is recommended. The temperature can be controlled by regulating the flow of hydrogen sulfide and by external cooling or heating as required.

Lab experiments have shown that good results can be obtained up to 80° C., however higher temperatures tend to induce color forming reactions.

(6) When the reaction is about 95% complete as indicated by gas chromatography (methyl-beta-mercaptopropionate will begin to appear) or infrared spectroscopy, the flow of hydrogen sulfide is stopped and the system is vented to a suitable hydrogen sulfide scrubber. It is then nitrogen sparged for one to two hours to remove dissolved hydrogen sulfide.

(7) After the nitrogen stripping step, the product is again analyzed by G.C. If the product contains more than 0.5% methyl-beta-mercaptopropionate then additional methyl acrylate is added (CA 2-3% of the original charge, but the exact percentage depends upon the analysis of the product.) The system is allowed to react for an additional two hours and the procedure repeated if required.

This control step adds great flexibility to the process and allows for the preparation of excellent dimethylthiodipropionate.

Work-up Procedures (8) The mixture is then cooled. The catalyst is neutralized with 85% phosphoric acid (two moles of $H_3PO_4$ for each mole of catalyst).

This is important and should be done as soon as possible, to prevent color formation.

(9) Diatomaceous earth filter aid (0.29% based on the weight of the product yield) is added and the mixture slurried for about one hour and the mixture is filtered. This will remove the catalyst as the salt.

Various techniques were explored for catalyst removal, including the use of commercial filter aids, such as Bright Sorb 30, which is a magnesium silicate, and diatomaceous earth. It was found that the best approach was to utilize phosphoric acid on a 2:1 mole basis of acid to catalyst, and then use a diatomaceous earth filtering aid to remove the reaction product by filtration. This system worked quite effectively and resulted in the formation of a good color product.

The invention is further illustrated by the following examples.

EXAMPLE 1

Addition of Hydrogen Sulfide to Methyl Acrylate— Conventional Preparation of Dimethylthiopropionate (Control)

Figure 8:
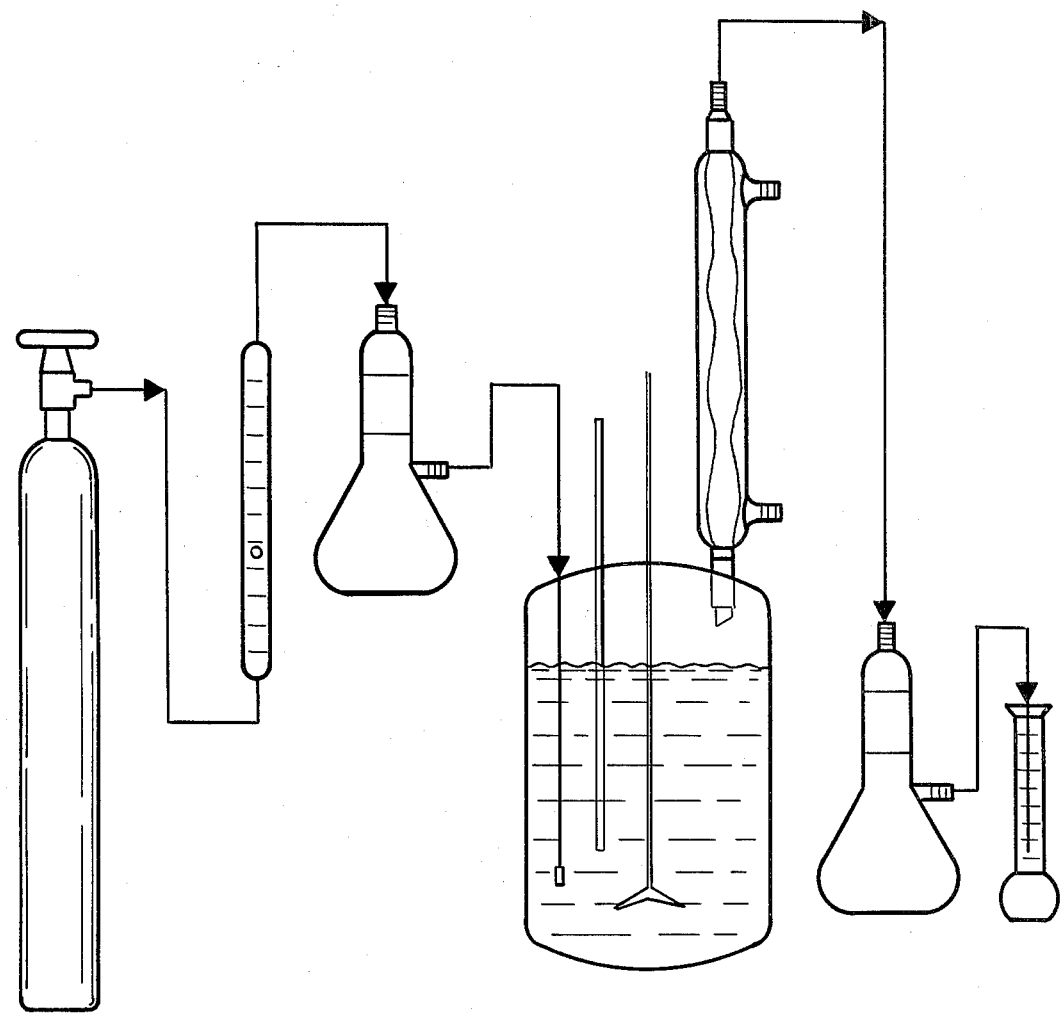
FIG. 8 is a schematic illustration of the laboratory apparatus described in Example 1 which was used to carry out the experiments of this application.

A four neck 1000 ml. reaction kettle was fitted with a mechanical stirrer, thermometer, gas dispersion tube, and a reflux condenser as illustrated in FIG. 8. A gas take off adapter was attached to the top of the condenser and connected by suitable tubing to an overflow trap and then to a bubble counter. A hydrogen sulfide cylinder was then connected to the system as shown in FIG. 8. The reactor was charged with 8 moles (689 g) of methyl acrylate. With stirring, the system was saturated with hydrogen sulfide. Sodium methoxide (as a 25% solution in methanol) was charged into the reactor. The level of active catalyst used was 0.2% (wt. percent) based on the methyl acrylate charge. It was added after saturation with hydrogen sulfide to minimize polymerization of the methyl acrylate by an anionic mechanism.

The reaction was allowed to exotherm to 70°-80° C. and the temperature was maintained by external cooling and by controlling the rate of addition of hydrogen sulfide. Samples were removed regularly to obtain a product distribution as a function of the extent of reaction.

FIG. 1 gives the product distribution. The gas chromatograph peak height of identified components were plotted versus percent reaction as determined by infrared analysis of the remaining methyl acrylate. Dimethylthiodipropionate (DMTDP) was plotted only as one-fourth of its actual peak height in order to use the same scale. MBMP is used to abbreviate methyl-beta-mercaptopropionate.

EXAMPLE 2

Figure 2:
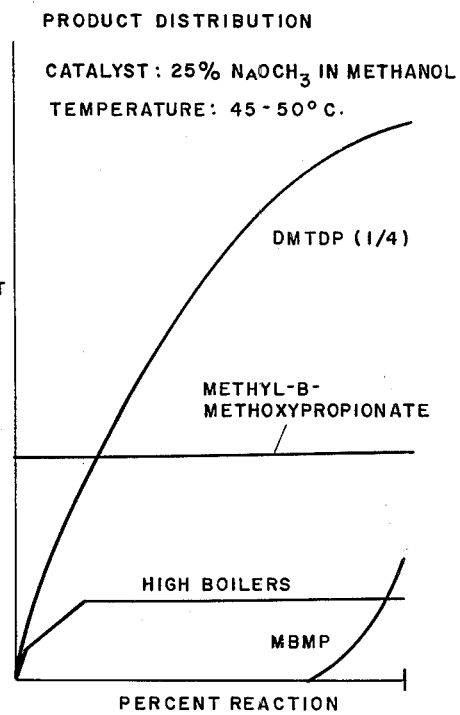
FIG. 2 illustrates the product distribution of Example 2.

Example 1 was repeated exactly, except that the temperature was controlled to 45°-50° C. The results are summarized in the FIG. 2 plots. This experiment shows that a marginal increase in selectivity was obtained by a decrease in temperature.

The Figure shows that relatively large quantities of undesirable side products occur using this catalyst.

EXAMPLE 3

Figure 3:
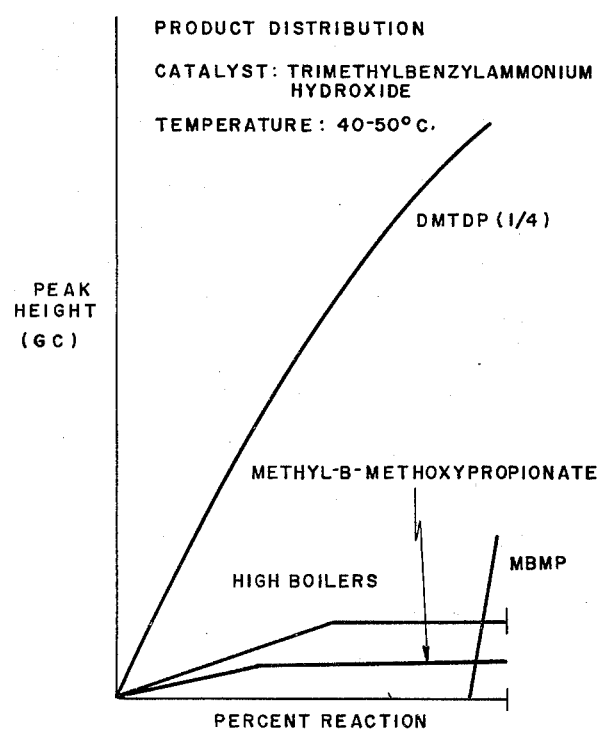
FIG. 3 shows a product distribution of a synthesis of DMTDP when another experimental catalyst was utilized in Example 3, but which did not meet the requirements of the inventive catalyst.

Example 2 was repeated exactly, except that the catalyst used was trimethylbenzylammonium hydroxide. This catalyst did not show any significant selectivity over the sodium methoxide system except that a decrease in methyl-beta-methoxy propionate was shown. See FIG. 3 which summarizes the analytical results.

EXAMPLE 4

Figure 4:
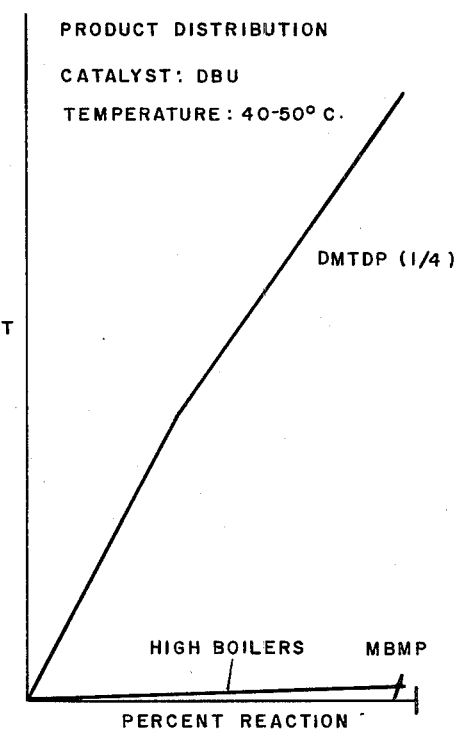
FIG. 4 is a illustration of the product distribution of DMTDP obtained when a catalyst of the invention was used in Example 4.

Example 2 was repeated exactly, except that 1,5-diazabicyclo (5.4.0) undec-5-ene (DBU) was used as a catalyst (0.2 wt. % based on methyl acrylate). This catalyst was surprisingly active and as can be seen from FIG. 4 in which the results are summarized, showed a significant increase in selectivity. The level of by-products and intermediate methyl-beta-mercaptopropionate is quite low.

EXAMPLE 5

Figure 5:
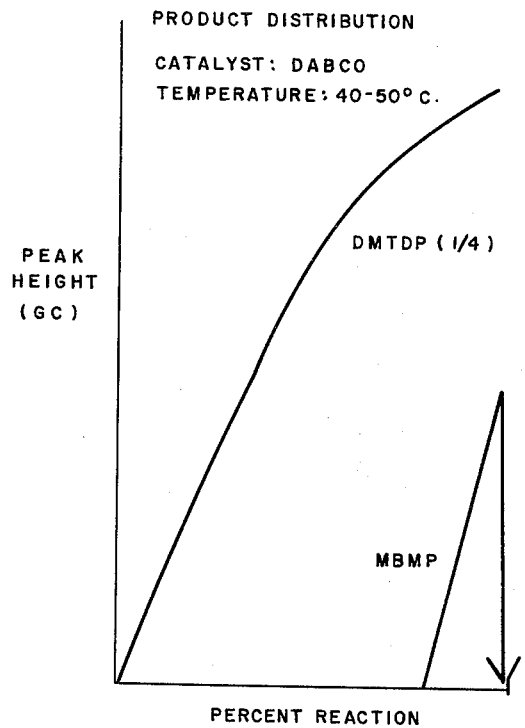
FIG. 5 is another product distribution diagram showing the improved results obtained when a catalyst of the invention was used in Example 5.

Example 2 was repeated exactly, except that 1,4-diazabicyclo (2.2.2) octane (DABCO) was used as a catalyst (0.2 wt. % based on methyl acrylate). As can be seen from FIG. 5 which summarizes the results, this catalyst showed marked selectivity. Further, it was found that the intermediate methyl-beta-mercaptopropionate could be removed by nitrogen sparging and by back addition of 1 to 3% excess methyl acrylate at the end of the reaction. The catalyst was then removed by adsorption on a suitable adsorbent, e.g., magnesium silicate filter aid and then by filtration. Alternatively, a salt was formed by addition of a suitable acid (phosphoric acid, p-toluene sulfonic acid, or others) and then filtering with a suitable filter aid.

EXAMPLE 6

Figure 6:
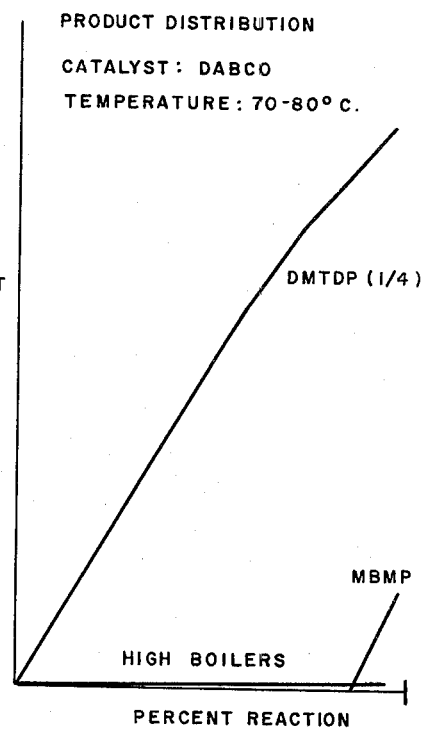
FIG. 6 shows the improved results of product distribution obtained when the preferred catalyst of the invention was used in Example 6.

Example 1 was repeated exactly, except that 1,4-diazabicyclo (2.2.2) octane (DABCO) was used as a catalyst at 0.2 wt. % level to methyl acrylate. FIG. 6 shows the selectivity of this system was greatly improved over the sodium methoxide system (as seen in FIG. 1).

EXAMPLE 7

Figure 7:
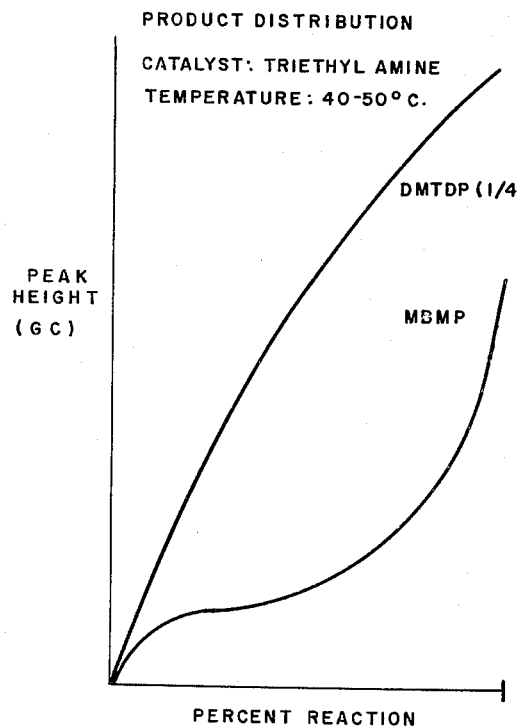
FIG. 7 shows the unsatisfactory results of product distribution obtained when an experimental catalyst not meeting the criteria of the inventive catalyst was utilized in Example 7.

Example 2 was repeated exactly, except that triethylamine was used as a catalyst. This catalyst showed very little activity as the 0.2 wt. % level. It was only at the 1 wt. % level that the reaction was reasonably rapid. FIG. 7 illustrating the use of this catalyst system shows that methyl-beta-mercaptopropionate (MBMP) was formed from the very start of this reaction and continued to build throughout the reaction to very high levels.

Pertinent references to this technology are as follows:
(1) Cornelio Caldo, Chim. Ind. 47 (3), 263-70 (1965) C.A. 63, 5526h.
(2) Milan Karvas et al. Czech 124, 771, Oct. 15, 1971 C.A. 69, 51641s.
(3) William F. Gresham and Myers F. Gribbins U.S. Pat. No. 2,468,725, May 3, 1949

(4) Leon L. Gershbein and Charles D. Hurd, J. Amer. Chem. Soc., 69, 241-2 (1947).
(5) Edward A. Fehnel and Marvin Carmack, Org. Syn., Coll. Vol. IV, 669-70 (1963).
(6) Takashi Otoba and Samio Teshirogi, Japan 17,368 (1965), Aug. 6, C.A. 64, P.C. 3362C.
(7) Henry G. Schutze and Delos E. Bown, U.S. Pat. No. 3,494,947, Feb. 10, 1970.

What is claimed is:
1. A process for the preparation of thioethers having the formula R'—S—R or R—S—R wherein R' is a $C_1$ to $C_{18}$ hydrocarbon ligand and R has the formula

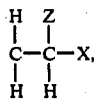

wherein Z is H or $CH_3$ and X is an electron withdrawing group selected from the group consisting of carboalkoxy, nitrile and carboxamide groups, said process comprising
(i) the exothermic reaction of an activated alpha, beta unsaturated compound of the formula

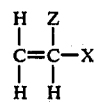

wherein Z is H or $CH_3$ and X is an electron withdrawing group selected from the group consisting of carboalkoxy, nitrile and carboxamide groups, said compound being capable of undergoing the Michael addition reaction, with at least stoichiometric quantities of $H_2S$ or R'SH in the presence of a catalyst and at a temperature in the range of 30° C. to 90° C., wherein, said catalyst is selected from the group consisting of
(a) 1,5-diazabicyclo (5,4,0) undec-5-ene,
(b) 1,4-diazabicyclo (2,2,2) octane,
(c) 1,5-diazabicyclo (4,3,0) non-5-ene, and
(d) quinuclidine, and
(ii) recovering said thioethers.
2. The process of claim 1 wherein said reaction is conducted by combining said compound with said catalyst and then adding said $H_2S$ or R'SH.
3. The process of claim 1 wherein said compound is selected from the group consisting of methyl acrylate, methyl methacrylate, ethyl acrylate, ethyl methacrylate and acrylonitrile.
4. The process of claim 3 wherein said compound is methyl acrylate.
5. The process of claim 3 wherein said compound is ethyl acrylate.
6. The process of claim 3 wherein said compound is acrylonitrile.
7. The process of claim 1 wherein said thioether is 3,3'-Dimethylthiodipropionate.
8. The process of claim 1 wherein said thioether is diethyl thiodipropionate.
9. The process of claim 1 wherein said thioether is 3,3' thiodipropionitrile.

* * * * *